(12) United States Patent
Hwang et al.

(10) Patent No.: US 10,960,040 B2
(45) Date of Patent: Mar. 30, 2021

(54) COMPOSITION FOR PREVENTING AND TREATING MUSCLE DISEASES OR IMPROVING MUSCULAR FUNCTION, CONTAINING PLATYCODON GRANDIFLORUM EXTRACT

(71) Applicant: Newtree Co., Ltd., Gyeonggi-do (KR)

(72) Inventors: Jae-Kwan Hwang, Seoul (KR); Mi-Bo Kim, Seoul (KR); Changhee Kim, Seoul (KR); Doun Kim, Gyeonggi-do (KR); Heechul Chung, Gyeonggi-do (KR)

(73) Assignee: NEWTREE CO., LTD., Gyeonggi-do (KR)

( * ) Notice: Subject to any disclaimer, the term of this patent is extended or adjusted under 35 U.S.C. 154(b) by 520 days.

(21) Appl. No.: 15/577,104

(22) PCT Filed: May 26, 2016

(86) PCT No.: PCT/KR2016/005586
§ 371 (c)(1),
(2) Date: Feb. 5, 2018

(87) PCT Pub. No.: WO2016/190683
PCT Pub. Date: Dec. 1, 2016

(65) Prior Publication Data
US 2018/0193396 A1  Jul. 12, 2018

(30) Foreign Application Priority Data
May 26, 2015 (KR) ........................ 10-2015-0072731

(51) Int. Cl.
| | | |
|---|---|---|
| *A61K 36/346* | (2006.01) | |
| *A21D 2/36* | (2006.01) | |
| *A61P 21/00* | (2006.01) | |
| *A61Q 19/00* | (2006.01) | |
| *A23L 33/105* | (2016.01) | |
| *A21D 13/80* | (2017.01) | |
| *A61K 8/9789* | (2017.01) | |
| *A23G 3/48* | (2006.01) | |
| *A23G 4/06* | (2006.01) | |
| *A23L 2/52* | (2006.01) | |
| *A61Q 19/08* | (2006.01) | |

(52) U.S. Cl.
CPC .............. *A61K 36/346* (2013.01); *A21D 2/36* (2013.01); *A21D 13/80* (2017.01); *A23G 3/48* (2013.01); *A23G 4/068* (2013.01); *A23L 2/52* (2013.01); *A23L 33/105* (2016.08); *A61K 8/9789* (2017.08); *A61P 21/00* (2018.01); *A61Q 19/00* (2013.01); *A61Q 19/007* (2013.01); *A23V 2002/00* (2013.01); *A61K 2236/33* (2013.01); *A61K 2236/37* (2013.01); *A61K 2800/10* (2013.01); *A61Q 19/08* (2013.01)

(58) Field of Classification Search
CPC . A21D 13/80; A21D 2/36; A23G 3/48; A23G 4/068; A23L 2/52; A23L 33/105; A23V 2002/00; A61K 2236/33; A61K 2236/37; A61K 36/346; A61K 8/9789; A61K 2800/10; A61Q 19/007; A61Q 19/00; A61Q 19/08; A61P 21/00
See application file for complete search history.

(56) References Cited

FOREIGN PATENT DOCUMENTS

| CN | 104208611 A | 12/2014 |
|---|---|---|
| KR | 20100120751 A | 11/2010 |
| KR | 1020100120751 A | 11/2010 |
| KR | 101034596 B1 * | 5/2011 |
| KR | 1020110061976 A | 6/2011 |
| KR | 1020110109607 A | 10/2011 |
| KR | 1020110140015 A | 12/2011 |

OTHER PUBLICATIONS

Zhang L, et al. "Platycodon grandijlorus—An Ethnopharmacological, phytochemical and pharmacological review" Journal of Ethnophannacology Apr. 22, 2015 (e-published Feb. 2, 2015),164,pp. 147-161; doi:10.1016/j.jep.2015.01.052. (Year: 2015).*

Zhang L, et al "Platycodon Grandiflorus—An Ethnopharmacological, Phytochemical and Pharmacological Review" J Ethnopharmacol. Apr. 22, 2015;164:147-61. doi: 10.1016/j.jep.2015.01.052. Epub Feb. 7, 2015. (Year: 2015).*

(Continued)

*Primary Examiner* — Aaron J Kosar
(74) *Attorney, Agent, or Firm* — Levenfeld Pearlstein, LLC (57) ABSTRACT

The present invention relates to a composition for preventing and treating muscle diseases or improving muscular function, containing a *Platycodon grandiflorum* extract. More specifically, the present invention relates to: a pharmaceutical composition for preventing and treating muscle diseases, containing a *Platycodon grandiflorum* extract; a food composition for preventing muscle diseases or improving muscular function; or a cosmetic for improving muscular function. The *Platycodon grandiflorum* extract of the present invention increases muscle formation by inducing muscular protein synthesis and muscle cell differentiation. Therefore, the extract is a natural product so as to be used safely without side effects, thereby being usable as an active ingredient of a pharmaceutical, food, or cosmetic composition exhibiting an excellent effect in preventing and treating muscle diseases or improving muscular function.

8 Claims, 3 Drawing Sheets
Specification includes a Sequence Listing.

(56) References Cited

OTHER PUBLICATIONS

International Search Report issued by ISA/KR in connection with PCT/KR2016/005586 dated Oct. 20, 2016.

Han, Gwang-Ho et al., Change of mTOR, p70S6K, 4E-BP1, and AMPK protein expressions with a intensive endurance exercise in rats, The Korea Journal of Sports Science, 2011, pp. 1551-1561, vol. 20, No. 3, Korea Institute of Sport Science, Korea.

Hornberger, Troy A., Mechanotransduction and the regulation of mTORC1 signaling in skeletal muscle, The International Journal of Biochemistry & Cell Biology, May 19, 2011, pp. 1267-1276, vol. 43, Elsevier Ltd., New York City, NY.

Bonaldo, Paolo et al., Cellular and molecular mechanisms of muscle atrophy, Disease Models & Mechanisms, 2013, pp. 25-39, vol. 6, The Company of Bilogists Ltd, United Kingdom.

Zanou, Nadege et al., Skeletal muscle hypertrophy and regeneration: interplay between the myogenic regulatory factors (MRFs) and insulin-like growth factors (IGFs) pathways, Cellular and Molecular Life Sciences, Apr. 4, 2013, pp. 4117-4130, vol. 70, Springer Basel, Switzerland.

Choi, Jae Ho et al., Platycodi Radix attenuates dimethylnitrosamine-induced liver fibrosis in rats by inducing Nrf2-mediated antioxidant enzymes, Food and Chemical Toxicology, Feb. 26, 2013, pp. 231-239, vol. 56, Elsevier Ltd., New York City, NY.

Lee, Chae Eun et al., Long-Term Consumption of Platycodi Radix Ameliorates Obesity and Insulin Resistance via the Activation of AMPK Pathways, Evidence-Based Complementary and Alternative Medicine, May 17, 2012, pp. 1-11, vol. 2012, Article ID 759143, Hindawi Publishing Corporation, South Korea.

Choi, Jae Ho et al., Platycodi Radix suppresses development of atopic dermatitis-like skin lesions, Environmental Toxicology and Pharmacology, Feb. 10, 2012, pp. 446-452, Vol. 33, Elsevier Ltd., New York City, NY.

Ahn, Young-Min et al., Platycodon grandiflorum modifies adipokines and the glucose uptake in high-fat diet in mice and L6 muscle cells, Journal of Pharmacy and Pharmacology, 2012, pp. 697-704, vol. 64, Royal Pharmaceutical Society.

Zhao, Xinyu, Study on skeletal muscle, fat and their associations with metabolic risk factors, China Academic Journal Electronic Magazine Co., Ltd., 2015, Issue 5, Zhejiang University.

\* cited by examiner

COMPOSITION FOR PREVENTING AND TREATING MUSCLE DISEASES OR IMPROVING MUSCULAR FUNCTION, CONTAINING PLATYCODON GRANDIFLORUM EXTRACT

TECHNICAL FIELD

The present application claims priority from Korean Patent Application No. 10-2015-0072731, filed on May 26, 2015, the entire contents of which are incorporated herein by reference.

The present invention relates to a composition for preventing and treating muscular diseases or improving muscular function containing a *Platycodon grandiflorum* (ballon flower; binomial nomenclature: *Platycodon grandiflorus*) extract. More particularly, the present invention relates to a pharmaceutical composition for preventing and treating muscular diseases, to a food composition for preventing and treating muscular diseases or improving muscular function, or to a cosmetic composition for improving muscular function.

BACKGROUND OF THE INVENTION

Muscle is the most abundant tissue in the human body, while being essential to maintain the functional capacity of the human body and to secure adequate muscle mass to prevent metabolic diseases. Muscle size is regulated by signaling pathways leading to anabolism or catabolism that occurs within the muscle. When more signal transduction leads to synthesis than to degradation of muscle proteins, the synthesis of muscle proteins is increased, resulting in muscle hypertrophy or hyperplasia (The Korea Journal of Sports Science, 20(3): 1551-1561, 2011).

Factors involved in muscle protein synthesis induce protein synthesis by phosphorylating downstream proteins based on the stimulation of phosphatidylinositol-3 kinase (PI3K)/Akt pathway in muscle cells. The activation of the mammalian target of rapamycin (mTOR) by PI3K/Akt signaling is recognized as a central growth signaling factor that integrates various growth signals in the cell. mTOR induces muscle protein synthesis by activating two factors that initiate mRNA translation, i.e. 4E-binding protein (4EBP1) and phosphorylated 70-kDa ribosomal S6 kinase (p70S6K), contributing to increase in muscle mass (The Korea Journal of Sports Science, 20 (3): 1551-1561, 2011; The International Journal of Biochemistry and Cell Biology, 43 (9): 1267-1276, 2011). Conversely, when the transcription factor forhead box (FoxO) migrates from the cytoplasm to the nucleus, it increases the expression of the E3 ubiquitin ligase, atrogin-1 and MuRF-1 which are involved in proteolysis (Disease Models and Mechanisms, 6:25-39, 2013). Increasing the expression level of these proteins promotes protein degradation in muscles, resulting in reduced muscle mass. Thus, the acceleration of mTOR activity and inhibition of atrogin-1 and MuRF-1 expression increase muscle mass by increasing the amount of muscle protein.

Muscle cell differentiation and muscle formation are regulated by a variety of muscle regulatory factors. Among them, MyoD initiates the expression of muscle specific genes and induces the differentiation of muscle satellite cells into myoblasts. Induction of myogenin expression by activation of MyoD is the most important factor in the fusion of myoblasts and is involved in the formation of myotube. The muscle fibers formed through this process are bundled to finally form muscles (Cellular and Molecular Life Sciences, 70: 4117-4130, 2013).

*Platycodon grandiflorum* is called "Doraji" in Korean as a plant of family Campanulaceae and genus *Platycodon* and its binominal nomenclature is *Platycodon grandiflorus*. *Platycodon grandiflorum* is widely distributed in East Asia including Korea, Japan, and China, and Saponin-type compounds are well known as its main ingredient. *Platycodon grandiflorum* is a traditional folk remedy that was used to treat such symptoms as cough, phlegm, fever, and diarrhea. Physiological activity of *Platycodon grandiflorum* was reported to include the inhibition of cirrhosis (Food and Chemical Toxicology, 56: 231-239, 2013), anti-obesity and the mitigation of insulin resistance (Evidence-Based Complementary and Alternative Medicine, 2012: 759143, 2012), the suppression of allergenic atopic dermatitis (Environmental Toxicology and Pharmacology, 33 (3): 446-452, 2012), and anti-cancer effect (International Journal of Hepatology, 38: 280-283, 2011). However, prior to the present invention, there has been no known effect of increasing the muscle mass in association with *Platycodon grandiflorum*.

Accordingly, the present inventors have found that a *Platycodon grandiflorum* extract increases muscle mass by its involvement in muscle formation through the synthesis of muscle proteins and the differentiation of muscle cells, thereby completing the present invention.

DETAILED DESCRIPTION OF THE INVENTION

Technical Problem

Accordingly, the inventors of the present invention have searched for a natural substance which has a superior activity of controlling muscle function and can safely be applied. As a result, the inventors verified that a *Platycodon grandiflorum* extract has an activity of preventing or treating muscle diseases or improving muscular function, thereby completing the present invention.

Accordingly, an aspect of the present invention is to provide a pharmaceutical composition for preventing or treating muscle diseases, the composition comprising a *Platycodon grandiflorum* extract as an active ingredient.

Another aspect of the present invention is to provide a food composition for preventing muscle diseases or improving muscle function, the composition comprising a *Platycodon grandiflorum* extract as an active ingredient.

Another aspect of the present invention is to provide a cosmetic composition for improving muscle function, the composition comprising a *Platycodon grandiflorum* extract as an active ingredient.

Still another aspect of the present invention is to provide a use of a *Platycodon grandiflorum* extract for preparing an agent for preventing or treating muscular diseases.

Still further aspect of the present invention is to provide a method for preventing or treating muscle diseases, the method comprising administering an effective amount of a *Platycodon grandiflorum* extract to a subject in need thereof.

Technical Solution

An embodiment according to an aspect of the present invention provides a pharmaceutical composition for preventing or treating muscle diseases, the composition comprising a *Platycodon grandiflorum* extract as an active ingredient.

An embodiment according to another aspect of the present invention provides a food composition for preventing muscle disease or improving muscle function, the composition comprising a *Platycodon grandiflorum* extract as an active ingredient.

An embodiment according to still another aspect of the present invention provides a cosmetic composition for improving muscle function, the composition comprising a *Platycodon grandiflorum* extract as an active ingredient.

An embodiment according to still further aspect of the present invention provides a use of a *Platycodon grandiflorum* extract for preparing an agent for preventing or treating muscle diseases.

An embodiment according to still further another aspect of the present invention provides a method for preventing or treating muscle diseases, the method comprising administering an effective amount of a *Platycodon grandiflorum* extract to a subject in need thereof.

Hereinafter, the present invention will be described in detail.

An embodiment according to an aspect of the present invention provides a pharmaceutical composition for preventing or treating muscle diseases, the composition comprising a *Platycodon grandiflorum* extract as an active ingredient.

The extract may be, but is not limited to, a subterranean part extract of *Platycodon grandiflorum*.

As used herein, the term 'muscle' refers collectively to the sinews, muscles, and tendons, while the term 'muscle function' refers to the ability of the muscle to exert its force by contraction of muscle. The muscle function includes muscular strength which is the ability of the muscle to exert its maximum contractility to overcome resistance, muscular endurance which is the ability of the muscle indicating how long or how many times the muscle can repeat contraction and relaxation on a given weight, and explosive muscular strength which is the ability of the muscle to exert a strong force in a short period of time. These muscle functions are managed by the liver and are proportional to muscle mass. The term 'the improvement of muscle function' refers to enhancement or betterment of muscle function.

As used herein, the composition for preventing or treating muscle diseases or for improving muscle function may contain a *Platycodon grandiflorum* extract alone and/or at least one kind of an active ingredient which exhibits a similar function to the *Platycodon grandiflorum* extract. The inclusion of additional ingredients may further enhance the effect of the composition of the present invention in improving muscle function. When the above additional ingredients are added, skin safety, easiness of formulation, and stability of effective ingredients may be considered according to the combined use.

The *Platycodon grandiflorum* extract of the present invention can be extracted by a known natural product extraction method. Preferably, one or more solvents are selected from the group consisting of water, organic solvents having 1 to 6 carbon atoms, and subcritical or supercritical fluids. The organic solvent having 1 to 6 carbon atoms may be selected from the group consisting of alcohol having 1 to 6 carbon atoms, acetone, ether, benzene, chloroform, ethyl acetate, methylene chloride, hexane, cyclohexane, and petroleum ether, but are not limited thereto.

Further, the *Platycodon grandiflorum* extract of the present invention can be obtained by extracting and purifying the subterranean part of dried *Platycodon grandiflorum* using purified water suitable for food processing, ethanol, supercritical carbon dioxide, or supercritical carbon dioxide. Alternatively, it can be obtained by separating and purifying the oil obtained by direct compression of the *Platycodon grandiflorum*. For example, the extract can be obtained by compressing the *Platycodon grandiflorum* under an ultra-high pressure condition of 100 Mpa or more. Preferably, the pressure may be in the range of 100 MPa to 1,000 Mpa which is an ultra-high pressure condition, but is not limited thereto.

For the purpose of being administered to the body of a subject, the composition according to the present invention may be prepared in the form of a pharmaceutical composition such as an oral formulation, a transdermal formulation, and an inhaled formulation, in the form of a food composition such as a functional food, a nutritional supplement, a health food and a food additive, or in the form of a cosmetic composition.

The *Platycodon grandiflorum* extract of the present invention is excellent in preventing or treating muscle diseases or improving muscular function In one example of the present invention, it was observed that methanol, hot water, ethanol, hexane, and ethyl acetate extracts were respectively prepared by using the subterranean part of *Platycodon grandiflorum* (see Example 1).

In another example of the present invention, it was found that the methanol extract of *Platycodon grandiflorum* effectively increased the expressions of p-mTOR, p-p70S6K in L6 muscle cells (see Examples 2 and 3).

In still another example of the present invention, it was shown that the hexane extract, it was shown that the ethyl acetate extract, the ethanol extract, and the hot water extract of *Platycodon grandiflorum* effectively increased the mRNA expression of MyoD and myogenin in L6 muscle cells, respectively (see Example 4).

In further example of the present invention, it was verified that the methanol extract of *Platycodon grandiflorum* effectively increased the mRNA expression of MyoD, myogenin in L6 muscle cells (see Example 5).

In still another example of the present invention, it was observed that the hexane extract, the ethyl acetate extract, the ethanol extract and the hot-water extract of *Platycodon grandiflorum* effectively reduced the mRNA expression of atrogin-1 and MuRF-1 in L6 muscle cells, respectively (see Example 6).

Therefore, the composition of the present invention has the effect of promoting the increase of the muscle mass, while the types of the muscle are not limited thereto. Increasing muscle mass is to improve muscle performance, especially, in the body composition. Muscle mass can be increased through physical exercise and endurance improvement, or by administering a muscle-enhancing substance to the body.

The *Platycodon grandiflorum* extract of the present invention has an excellent activity for increasing muscle mass, and thus can be used as an effective ingredient of a pharmaceutical composition.

In addition, the *Platycodon grandiflorum* extract of the present invention has an excellent activity of increasing muscle mass, and thus can be used as an effective ingredient of a food composition.

In addition, the *Platycodon grandiflorum* extract of the present invention has an excellent activity for increasing muscle mass, and thus can be used as an effective ingredient of a cosmetic composition.

The pharmaceutical composition of the present invention can contain a pharmaceutically acceptable salt of the *Platycodon grandiflorum* extract. As used herein, the term 'pharmaceutically acceptable' refers to those that are physiologically acceptable and do not normally cause an allergic reaction or similar reaction when administered to humans, wherein the salt is preferably an acid addition salt formed by a pharmaceutically acceptable free acid.

The pharmaceutically acceptable salt of the *Platycodon grandiflorum* extract may be an acid addition salt formed using an organic acid or an inorganic acid. The organic acid may be, for example, formic acid, acetic acid, propionic acid, lactic acid, butyric acid, isobutyric acid, trifluoroacetic acid, malic acid, maleic acid, malonic acid, fumaric acid, succinic acid, succinic monoamide, glutamic acid, tartaric acid, oxalic acid, citric acid, glycolic acid, glucuronic acid, ascorbic acid, benzoic acid, phthalic acid, salicylic acid, anthranilic acid, dichloroacetic acid, aminooxyacetic acid, benzenesulfonic acid, p-toluenesulfonic acid or methanesulfonic acid. The inorganic acid comprises, for example, hydrochloric acid, bromic acid, sulfuric acid, phosphoric acid, nitric acid, carbonic acid or boric acid. The acid-addition salt may preferably be in the form of a hydrochloride or acetate, more preferably in the form of a hydrochloride.

The above mentioned acid-addition salts may be prepared by conventional salt preparation methods such as a) directly mixing the *Platycodon grandiflorum* extract and an acid, b) dissolving one of them in a solvent or a water-containing solvent, followed by mixing, and c) placing the *Platycodon grandiflorum* extract in a solvent or an acid in a hydrated solvent, followed by mixing.

Apart from the above, additional salt forms include the salts of gamma-aminobutyric acid (GABA), gabapentin, pregabalin, nicotinate, adipate, hemimarate, cysteine, acetylcysteine, methionine, arginine, lysine, ornithine or aspartate.

In addition, the pharmaceutical composition of the present invention for preventing and treating muscle disease may further comprise a pharmaceutically acceptable carrier.

The pharmaceutically acceptable carrier may further include, for example, a carrier for oral or parenteral administration. Carriers for oral administration may include lactose, starch, cellulose derivatives, magnesium stearate, stearic acid, and the like. Carriers for parenteral administration may include water, suitable oils, saline, aqueous glucose and glycols and the like. In addition, stabilizers and preservatives may be further included. Suitable stabilizers may be antioxidants such as sodium hydrogen sulfite, sodium sulfite and ascorbic acid. Suitable preservatives may include benzalkonium chloride, methyl- or propyl-paraben and chlorobutanol. Other pharmaceutically acceptable carriers may be referred to those described in the following reference (Remington's Pharmaceutical Sciences, 19th ed., Mack Publishing Company, Easton, Pa., 1995).

The pharmaceutical composition of the present invention can be administered to mammals including humans by any method. For example, it can be administered orally or parenterally, while parenteral administration methods may include, but are not limited to, intravenous, intramuscular, intra-arterial, intramedullary, intrathecal, intracardiac, transdermal, subcutaneous, peritoneal, intranasal, enteral, topical, sublingual or rectal administration.

The pharmaceutical composition of the present invention may be formulated into oral or parenteral dosage forms according to the route of administration as described above. When formulated, it is prepared by one or more buffers (e.g., saline or PBS), antioxidants, bacteriostats, chelating agents (e.g., EDTA or glutathione), fillers, extenders, binders, adjuvants (e.g., aluminum hydroxide), suspending agents, thickening agents, wetting agents, disintegrating agents or surfactants, diluents or excipients.

Solid formulations for oral administration include tablets, pills, powders, granules, solutions, gels, syrups, slurries, suspensions or capsules. These solid formulations can be prepared by mixing the pharmaceutical composition of the present invention with at least one excipient, for example, starch (including corn starch, wheat starch, rice starch and potato starch), calcium carbonate, sucrose, lactose, dextrose, sorbitol, mannitol, xylitol, erythritol maltitol, cellulose, methyl cellulose, sodium carboxymethyl cellulose and hydroxypropylmethyl-cellulose or gelatin. For instance, tablets or sugar-coated tablets can be obtained by combining the active ingredient with a solid excipient, then milling it, adding suitable auxiliaries, and processing the mixture into granules.

In addition to simple excipients, lubricants such as magnesium, stearate talc are also used. Liquid preparations for oral administration include suspensions, solutions, emulsions or syrups. In addition to commonly used simple diluents such as water or liquid paraffin, various excipients such as wetting agents, sweetening agents, fragrances or preservatives may be included.

In addition, crosslinked polyvinylpyrrolidone, agar, alginic acid or sodium alginate may be added as a disintegrant depending on formulations, and may further include an anti-coagulant, a lubricant, a wetting agent, a fragrance, an emulsifier and an antiseptic agent.

When administered parenterally, the pharmaceutical composition, of the present invention can be formulated in accordance with methods known in the art in the form of injections, transdermal agents, and nasal inhalers, together with suitable parenteral carriers. In the case of the injections, they must be sterilized and protected from, contamination of microorganisms such as bacteria and fungus. Examples of suitable carriers for injectable formulations include, but are not limited to, solvents or dispersion media containing water, ethanol, polyols (such as glycerol, propylene glycol and liquid polyethylene glycol, etc.), mixtures thereof and/or vegetable oils. More preferably, suitable carriers include, but are not limited to, Hank's solution, Ringer's solution, phosphate buffered saline (PBS) containing triethanolamine or sterile water for injection, 10% ethanol, 40% propylene glycol and 5% dextrose. To protect the injection from microbial contamination, various antibacterial and antifungal agents such as parabens, chlorobutanol, phenol, sorbic acid, and thimerosal may be further included. Alternatively, the injectable formulation may mostly further contain an isotonic agent, such as sugar or sodium chloride.

Examples of transdermal dosage forms include ointments, creams, lotions, gels, solutions for external use, pastes, liniments, and aerosols. The transdermal administration means that a pharmaceutical composition is topically administered to the skin, whereby an effective amount of the active ingredient contained in the pharmaceutical composition is delivered into the skin.

In the case of an inhalation dosage form, the compound used in accordance with the present invention may be conveniently delivered in the form of an aerosol spray from a pressurized pack or nebulizer, while using a suitable propellant, such as dichlorofluoromethane, trichlorofluoromethane, dichlorotetrafluoroethane, carbon dioxide and other suitable gas. In the case of a pressurized, aerosol, the dosage unit may be determined by providing a valve that delivers a metered amount. For example, gelatin capsules and cartridges used for an inhaler or insufflator may be formulated to contain a compound, and a powder mixture of a suitable powder base such as lactose or starch. Formulations for parenteral administration are described in the literature (Remington's Pharmaceutical Science, 15th Edition, 1975. Mack Publishing Company, Easton, Pa. 18042, Chapter 87: Blaug, Seymour) as a generally known form of pharmaceutical chemistry.

The pharmaceutical composition according to the present invention for the prevention and treatment of muscle diseases of the present invention can provide a desirable preventative and therapeutic effects for muscle diseases when the *Platycodon grandiflorum* extract is contained in its effective amount. As used herein, 'the effective amount' refers to an amount that exhibits an effect greater than that of the negative control, and preferably refers to an amount sufficient to improve muscle function. The pharmaceutical composition of the present invention may contain 0.01 to 99.99% of the *Platycodon grandiflorum* extract, while the remaining amount may be a pharmaceutically acceptable carrier. The effective amount of the *Platycodon grandiflorum* extract contained in the pharmaceutical composition of the present invention will vary depending on a form into which the composition is formulated or the like.

The total effective amount of the pharmaceutical composition of the present invention may be administered to a patient in a single dose and may be administered by a fractionated treatment protocol administered over a prolonged period of time in multiple doses. The pharmaceutical composition of the present invention may vary in the content of the active ingredient depending on the severity of the disease. When administered parenterally, it is preferably administered in an amount of 0.01 to 50 mg, more preferably 0.1 to 30 mg per 1 kg of body weight per day on the basis of the *Platycodon grandiflorum* extract. When administered orally, it may be administered in one to several divided doses so as to be preferably administered in an amount of 0.01 to 100 mg, more preferably 0.01 to 10 mg per kg of body weight per day on the basis of the *Platycodon grandiflorum* extract. However, the dose of the *Platycodon grandiflorum* extract is determined depending on various factors including the route of administration and the number of treatments of the pharmaceutical composition as well as the patient's age, body weight, health condition, sex, severity of disease, diet and excretion rate. Accordingly, those of ordinary skill in the art will be able to determine the appropriate effective dose for the particular use for the prevention and treatment of muscle diseases. The pharmaceutical composition according to the present invention is not particularly limited to formulations, administration routes and administration methods as long as the effect of the present invention is exhibited.

The pharmaceutical composition according to the present invention for the prevention and treatment of muscle diseases can be used alone or in combination with methods using surgery, radiation therapy, hormone therapy, chemical therapy or a biological response modifier.

The pharmaceutical composition according to the present invention for the prevention and treatment of muscle diseases can also be provided as a formulation of an external agent containing the *Platycodon grandiflorum* extract as an active ingredient.

When the pharmaceutical composition of the present invention for the prevention and treatment of muscle diseases is used as an external preparation for skin, it may further contain adjuvants commonly used in the field of dermatology, for instance any ingredients conventionally used in dermatological external preparations such as fatty substances, organic solvents, solubilizers, thickening agents, gelling agents softeners, antioxidants, suspending agents, stabilizers, foaming agents, fragrant agents, surfactants, water, ionic emulsifiers, non-ionic emulsifiers, fillers, sequestering agents, chelating agents, preservatives, vitamins, blocking agents, wetting agents, essential oils, dyes, pigments, hydrophilic active agents, lipophilic active agents, lipids vesicles and the like. Such components may be contained in amounts commonly used in the field of dermatology.

When the pharmaceutical composition of the present invention for the prevention and treatment of muscle diseases is provided as an external preparation for skin, it may be formulated into such a formulation as ointments, patches, gels, creams, and sprays, but may not be limited thereto.

The composition of the present invention for preventing muscle diseases and improving muscle function may also be a food composition. In the case where the composition of the present invention for preventing muscle diseases and improving muscle function is used as a food composition, it can be used for prevention or improvement of muscle diseases due to muscle wasting or degeneration. It has been reported that muscle wasting and degeneration may be caused by genetic factors, acquired factors, or aging. Muscle wasting is characterized by gradual loss of muscle mass, weakness and degeneration of muscles, especially skeletal muscles or voluntary muscles and heart muscles. Examples of such diseases include atony, muscular atrophy, muscular dystrophy, muscle degeneration, myasthenia, cachexia, sarcopenia and the like. The composition of the present invention has an effect of increasing muscle mass, while the types of muscle are not limited.

The food composition of the present invention includes all forms of functional foods, nutritional supplements, health foods, food additives and feeds for consumption by humans or animals including livestock. Such types of Food compositions may be prepared in a variety of forms according to conventional methods known in the art.

The food compositions can be prepared in a variety of forms according to conventional methods known in the art. The *Platycodon grandiflorum* extract may be added into common foods which include, but are not limited to, beverages (e.g., alcoholic beverages), fruits and processed foods thereof (e.g., canned fruits, bottled jam, and marmalade), fish, meat and processed foods thereof (e.g., ham and corn beef sausage), breads and noodles (e.g., udon, buckwheat noodles, ramen noodles, spaghetti, and macaroni), juice, various drinks, cookies, taffy, dairy product (e.g., butter and cheese), edible vegetable oil, margarine, vegetable protein, retort food, frozen food, and various kinds of seasoning (e.g., soybean paste, soy sauce, and sauce). The *Platycodon grandiflorum* extract may be added into nutritional supplements which include, but are not limited to, capsules, tablets, and pills. In addition, the health functional food may be prepared, but are not limited to, by liquifying, granulating, encapsulating or pulverizing the *Platycodon grandiflorum* extract so that the *Platycodon grandiflorum* extract itself can be prepared in the form of teas, juices, and drinks for consumption. In addition, in order to use the *Platycodon grandiflorum* extract as a food additive, it may be used in the form of powder or concentrated liquid. Furthermore, it can be prepared in the form of a composition by mixing together the *Platycodon grandiflorum* extract and a known active ingredient effective in the prevention of muscle diseases and improvement of muscle function.

When the composition of the present invention for preventing muscle diseases and improving muscle function is used as a health beverage composition, the health beverage composition may contain various flavors or natural carbohydrates as additional ingredients as in conventional beverages. The above-mentioned natural carbohydrates include monosaccharides such as glucose and fructose; disaccharides such as maltose and sucrose; polysaccharides such as dextrins and cyclodextrins; sugar alcohols such as Xylitol, sorbitol, and erythritol. Sweeteners include natural sweeteners such as the extracts of thaumatin and stevia; synthetic sweeteners such as saccharin and aspartame. The ratio of the natural carbohydrate is generally about 0.01 g to 0.04 g, preferably about 0.02 g to 0.03 g per 100 mL of the composition of the present invention.

The *Platycodon grandiflorum* extract may be contained as an active ingredient of a food composition for the prevention of muscle diseases and improvement of muscle function. The effective amount thereof is preferably, but is not particularly limited to, 0.01% to 100% of the total weight of the composition. The food composition of the present invention may be prepared by mixing the *Platycodon grandiflorum* extract and other active ingredients known to be effective in preventing muscle diseases and improving muscle function.

In addition, the health food of the present invention may contain various nutrients, vitamins, electrolytes, flavors, colorants, pectic acid, salts of pectic acid, alginic acid, salts of alginic acid, organic acid, protective colloid thickener, pH adjuster, stabilizer, glycerin, an alcohol or a carbonating agent. In addition, the health food of the present invention may contain pulps for the production of natural fruit juice, fruit juice drink or vegetable drink. These components may be used independently or in combination. The proportion of such additives is not critical, but is generally selected in the range of 0.01 to 0.1 parts by weight per 100 parts by weight of the composition of the present invention.

The composition for improving muscle function of the present invention may also be a cosmetic composition. The cosmetic composition of the present invention contains the *Platycodon grandiflorum* extract as an active ingredient and may be prepared into basic cosmetic composition (e.g., lotion, cream, essence, cleanser such as cleansing foam and cleansing water, pack, and body oil), color cosmetic composition (e.g., foundation, lipstick, mascara, and make-up base), hair product composition (e.g., shampoo, rinse, hair conditioner, and hair gel) and soap together with dermatologically acceptable excipients.

Such excipients include, but are not limited to, for example, emollients, skin penetration enhancers, colorants, fragrants, emulsifiers, thickeners, and solvents. In addition, it may further contain perfumes, coloring matters, bactericides, antioxidants, preservatives, and moisturizers, and may include thickeners, inorganic salts, and synthetic polymeric substances for the purpose of improving physical properties. For example, when cleansers and soap are prepared with the cosmetic composition of the present invention, they may be easily prepared by adding the *Platycodon grandiflorum* extract to a common cleanser and a soap base. In the case of producing a cream, it can be prepared, by adding the *Platycodon grandiflorum* extract or its salt to a cream base of a typical underwater type (O/W). A synthetic or natural material such as a protein, a mineral, or a vitamin may be further added for the purpose of improving physical properties with a flavor, a chelating agent, a pigment, an antioxidant, and an antiseptic.

The content of the *Platycodon grandiflorum* extract contained in the cosmetic composition of the present invention is not limited thereto, but is preferably 0.001 to 10% by weight, more preferably 0.01 to 5% by weight based on the total weight of the whole composition. If the content is less than 0.001% by weight, the desired anti-aging or wrinkle-reducing effect may not be expected. If the content is more than 10% by weight, it may be difficult to manufacture in terms of safety or preparation of formulation.

The present invention provides use of the *Platycodon grandiflorum* extract for preparing an agent for preventing or treating muscle diseases.

The present invention provides a method for preventing or treating muscle diseases, the method comprising administering an effective amount of the *Platycodon grandiflorum* extract to a subject in need thereof.

The term "effective amount" of the present invention refers to an amount that, when administered to a subject, leads to the improvement, treatment, or prevention of muscle diseases. The term "subject" may be an animal, preferably a mammal including humans and livestock, animal-derived cells, tissues, or organs. The subject may be a patient or livestock needed for treatment.

Effects of the Invention

The *Platycodon grandiflorum* extract of the present invention activates mTOR, p70S6K, MyoD, and myogenin, leading to the synthesis of muscle proteins and the differentiation of muscle cells to increase muscle formation. Therefore, the *Platycodon grandiflorum* extract of the present invention is a natural product, and thus can be safely used without side effects, while providing a composition exhibiting an excellent effect for preventing or treating muscle diseases or improving muscle function.

MODE FOR CARRYING OUT INVENTION

Hereinafter, the present invention will be described in more detail with reference to Examples.

However, the following examples are illustrative of the present invention, and the present invention is not limited to the following examples.

Example 1

Preparation of the *Platycodon grandiflorum* Extract

<1-1> Preparation of the Methanol Extract of *Platycodon grandiflorum*

The subterranean part of dried *Platycodon grandiflorum* was pulverized with a mixer, and 100 g of the milled *Platycodon grandiflorum* sample was added to 1 L of 100% methanol and extracted at room temperature for 48 hours. The extracted sample was filtered with Whatman No. 2 filter paper, and the filtered extract was concentrated using a vacuum rotary condenser to remove the solvent component, and then a methanol extract of *Platycodon grandiflorum* was obtained.

<1-2> Preparation of the Ethanol Extract of *Platycodon grandiflorum*

The subterranean part of *Platycodon grandiflorum* was pulverized with a mixer, and 100 g of the milled *Platycodon grandiflorum* sample was added to 1 L of 100% ethanol and extracted at room temperature for 48 hours. The extracted sample was filtered with Whatman No. 2 filter paper, and the filtered extract was concentrated with, a vacuum rotary condenser to remove the solvent components, and then an ethanol extract of *Platycodon grandiflorum* was obtained.

<1-3> Preparation of the Ethyl Acetate Extract of *Platycodon grandiflorum*

The subterranean part of the dried *Platycodon grandiflorum* was pulverized with a mixer, and 100 g of milled *Platycodon grandiflorum* sample was added to 1 L of 100% ethyl acetate and extracted at room temperature for 48 hours. The extracted sample was filtered with Whatman No. 2 filter paper, and the filtered extract was concentrated with a vacuum rotary condenser to remove solvent components to obtain an ethyl acetate extract of *Platycodon grandiflorum*.

<1-4> Preparation of the Hexane Extract of *Platycodon grandiflorum*

The subterranean part of the dried *Platycodon grandiflorum* was pulverized with a mixer, and 100 g of milled *Platycodon grandiflorum* sample was added, to 1 L of 100% hexane and extracted at room temperature for 48 hours. The extracted sample was filtered, with Whatman No. 2 filter paper, and the filtered extract was concentrated with a vacuum rotary condenser to remove solvent components, and then a hexane extract of *Platycodon grandiflorum* was obtained.

<1-5> Preparation of the Hot-Water Extract of *Platycodon grandiflorum*

The subterranean part of the dried *Platycodon grandiflorum* was pulverized with a mixer, and 100 g of the milled *Platycodon grandiflorum* sample was added to 1 L of water and extracted while stirring at 100° C. for 2 hours. The extracted sample was filtered with Whatman No. 2 filter paper, and the filtered extract was concentrated with a vacuum rotary condenser to remove solvent components, and then a hot-water extract of *Platycodon grandiflorum* was obtained.

<1-6> Preparation of the Ultra-High Pressure Extract of *Platycodon grandiflorum*

The subterranean part of the dried *Platycodon grandiflorum* was pulverized with a mixer, 1 g of the milled *Platycodon grandiflorum* sample and 76 ml of 18% ethanol were placed in a polyethylene pack and sealed, and then extracted with an ultra-high pressure extraction apparatus (Frescal MFP-7000; Mitsubishi Heavy Industries, Tokyo, Japan). Extraction pressure was 320 MPa and extraction time was 5 min. The extracted sample was filtered with Whatman No. 2 filter paper, and the filtered extract was concentrated with a vacuum rotary condenser to remove solvent components to obtain an ultra-high pressure extract of *Platycodon grandiflorum*.

<1-7> Preparation of the Supercritical Fluid Extract of *Platycodon grandiflorum*

The dried *Platycodon grandiflorum* was pulverized with a mixer, and 1 g of the milled *Platycodon grandiflorum* sample was filled into a sample cartridge and extracted with a supercritical fluid extraction apparatus (SFX 3560, Isco Inc., Lincoln, Nebr., USA). Supercritical fluid extraction conditions were extraction pressure 40 MPa, extraction temperature 50° C., supercritical carbon dioxide flow rate 60 mL/min, and extraction time 60 min. When the supercritical fluid extraction was completed, the supercritical fluid condition was released by lowering the pressure of the extraction device to obtain a supercritical fluid extract of *Platycodon grandiflorum*.

<1-8> Preparation of the Subcritical Fluid Extract of *Platycodon grandiflorum*

The dried *Platycodon grandiflorum* was pulverized with a mixer, and 1 g of milled. *Platycodon grandiflorum* sample was added to 10 mL of distilled water and extracted with a subcritical fluid extractor (DIONEX Accelerated Solvent Extractor 100, DIONEX co., USA). The subcritical fluid extraction condition was extraction pressure 2.5 MPa, the extraction temperature 150° C., and the extraction time 15 minutes. The extracted sample was filtered with Wattman No. 2 filter paper, and the filtered extract was lyophilized at −40° C. to obtain a subcritical fluid extract of *Platycodon grandiflorum*.

Example 2

Effect of *Platycodon grandiflorum* Extract on Increasing the Synthesis of Muscle Proteins Muscle cell L6 myoblasts (ATCC, Manassas, Va., USA) were added to a 6-well plate with Dulbecco's modified Eagle's Media (DMEM; Hyclone) containing 10% fetal bovine serum (FBS; Hyclone, Logan, Utah, USA) at a concentration of $1 \times 10^5$ cells/ml. When, the cell density reached about 80 to 85%, the medium in the wells was removed, and 10 μg/mL of the *Platycodon grandiflorum* extract of Examples 1-1 to 1-5, respectively, were added to DMEM containing 2% horse serum (HS; Hyclone) for the purpose of inducing myotube differentiation. Meanwhile, a group treated with 0.01% DMSO instead of the sample extract was used as a control group. This process was carried out for 6 days in two days to differentiate and then dissolved in NP-40 buffer solution (ELPIS-Biotech, Daejeon, Republic of Korea) containing proteinase inhibitor cocktail. The cells dissolved in the buffer solution were transferred to a 1.5 ml tube and centrifuged at 13,000 rpm for 10 minutes to take only a supernatant. The supernatant was quantified using the Bradford method (Bio-Rad Laboratories Inc., Hercules, Calif., USA). The quantified proteins were boiled for 5 minutes, separated by electrophoresis on 10% SDS-PAGE, and the separated, proteins were transferred to the nitrocellulose membrane. p-mTOR primary antibodies (Cellular signaling technology, Beverly, Mass., USA) were diluted with 2.5% bovine serum albumin (BSA) at a ratio of 1:1000 and reacted with proteins transferred to the nitrocellulose membrane for 20 hours at room temperature. The nitrocellulose membrane incubated with the diluted primary antibodies was washed three times for 10 minutes using Tris-buffer Saline Tween 20 (TEST). After-washing, the anti-rabbit secondary antibodies (Bethyl Laboratories, Inc., Montgomery, Tex., USA) conjugated with horseradish peroxidase, which recognizes the primary antibodies, were diluted to 1:5000 in 2.5% BSA, followed by reacting with the nitrocellulose membrane at room temperature for 2 hours and washing three times for 10 minutes using TBST. Protein bands were developed using ECL western, blotting detection reagents (Amersham, Tokyo, Japan), while the developed protein bands were identified using G:BOX EE imaging system (Syngene, Cambridge, UK). The results are shown in FIG. 1.

Figure 1:
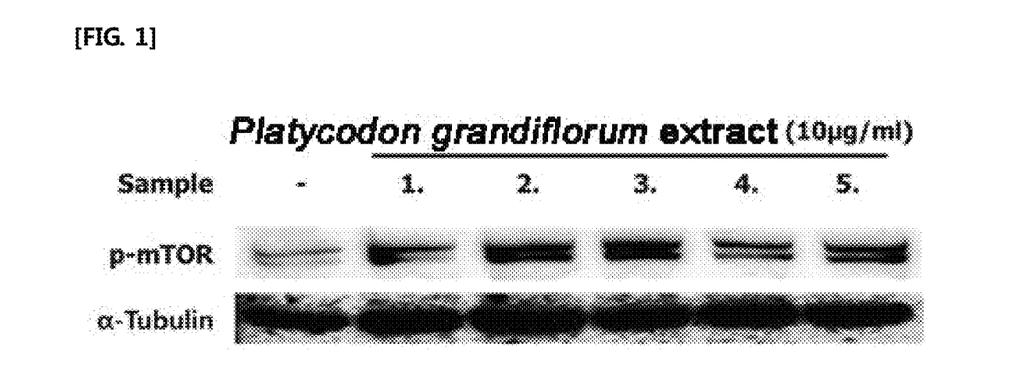
FIG. 1 shows the results of measuring the expression of p-mTOR protein in L6 muscle cells by using five kinds of the *Platycodon grandiflorum* extract (1. methanol extract, 2. ethanol extract, 3. ethyl acetate extract, 4. hexane extract and 5. hot water extract), respectively.

As shown, in FIG. 1, it was confirmed that the expression level of p-mTOR in L6 muscle cells was increased by the treatment of the *Platycodon grandiflorum* extract. This verifies that the *Platycodon grandiflorum* extract of the present invention is excellent in increasing the production of muscle in muscle cells.

Example 3

Figure 2:
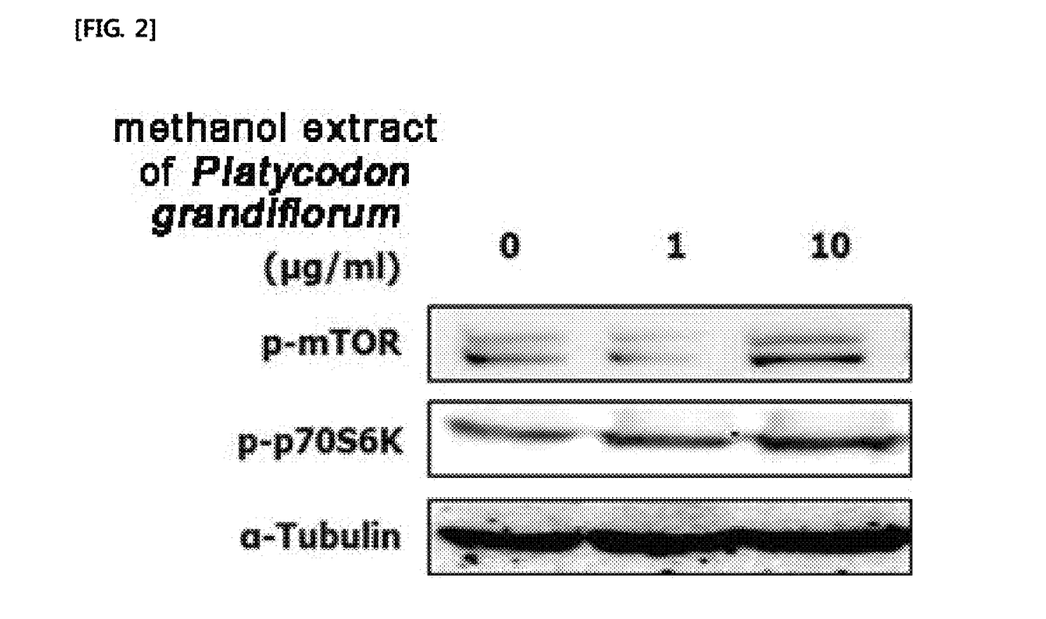
FIG. 2 shows the results of measuring the expression of p-mTOR and p-p70S6K proteins in L6 muscle cells by using the methanol extract of *Platycodon grandiflorum*, respectively.

Effect of the Methanol Extract of *Platycodon grandiflorum* on Increasing the Synthesis of Muscle Proteins Experiments were conducted in the same manner as in Example 2, except that the methanol extract of *Platycodon grandiflorum* of Example 1-1 was used at a concentration of 1 µg/ml and 10 µg/ml. The protein band was confirmed by reacting with p-mTOR primary antibodies (Cell signaling technology) and p-p70S6K antibodies (Santa Cruz Biotechnology, Santa Cruz, Calif., USA).

As shown in FIG. 2, it was observed that the expression of p-mTOR and p-p70S6K was increased respectively in L6 muscle cells by treating the methanol extract of *Platycodon grandiflorum*. This verifies that the methanol extract of *Platycodon grandiflorum* of the present invention is excellent in increasing the production of muscle in muscle cells.

Example 4

Effect of *Platycodon grandiflorum* Extract on Muscle Differentiation

Figure 3:
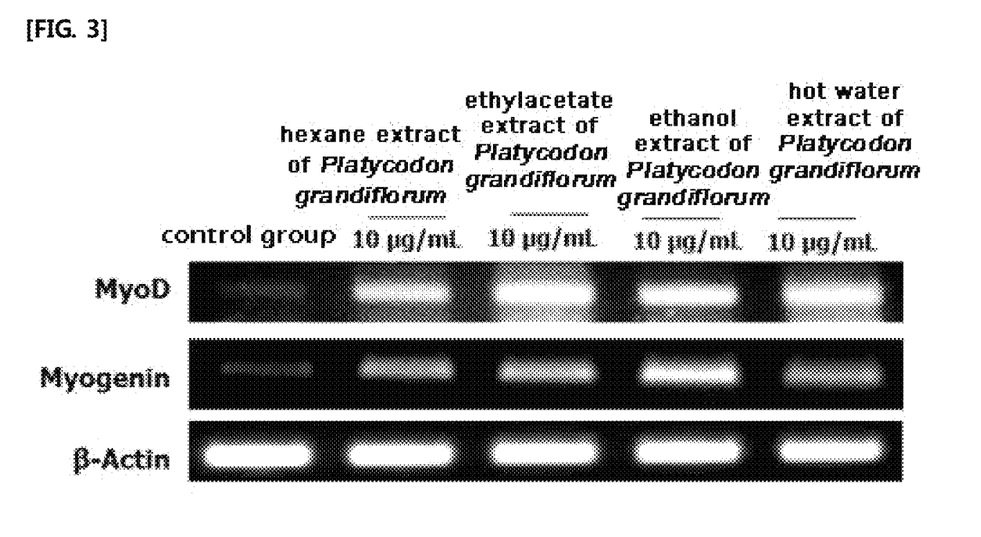
FIG. 3 shows the results of measuring the mRNA expression of MyoD and myogenin, respectively, by treating the hexane extract, the ethyl acetate extract, the ethanol extract, and the hot water extract of *Platycodon grandiflorum* s.

Muscle cells, L6 myoblasts (ATCC) were added to a 6-well plate at $2\times10^5$ cells/ml together with DMEM (Hyclone) containing 10% FBS (Hyclone). When the cell density reached about 80 to 85%, the medium in the wells was removed. The cells were treated with the hexane extracts, the ethylacetate extract, the ethanol extract and the hot water extract of *Platycodon grandiflorum* prepared in Examples 1-2 to 1-5, respectively, dissolved in DMEM (Hyclone) containing 2% HS (Hyclone) at a concentration of 10 µg/mL to induce myotube differentiation. Meanwhile, a group treated with 0.01% DMSO instead of the sample extract was used as a control group. This procedure was carried out for 6 days in two days to differentiate and total RNA was isolated using TRIzol reagent (Invitrogen, Carlsbad, Calif., USA). The isolated total RNA was quantified using NanoDrop 1000 (Thermo Fisher Scientific Inc., Mass., USA). Quantified 16 µL of RNA was synthesized into cDNA using Reverse Transcriptase Premix (ELPIS-Biotech) and PCR machine (Gene Amp PCR System 2700; Applied Biosystems, Mass., USA) at 42° C. for 55 minutes and 70° C. for 15 minutes. 4 µL out of 16 µL cDNA was amplified by PCR using the following specific primers (Bioneer, Daejeon, Republic of Korea) and PCR premix (ELPIS-Biotech). PCR was performed by repeating 30 cycles of 95° C. for 30 seconds, 60° C. for 1 minute, and 72° C. for 1 minute.

MyoD
(SEQ ID NO: 1)
Forward primer: 5'-TTTCGACTCACCAGACCTGC-3'

(SEQ ID NO: 2)
Reverse primer: 5'-CAGAGCCTGCAGACCTTCAA-3'

Myogenin
(SEQ ID NO: 3)
Forward primer: 5'-TTTCGCACCTGATGGACCTG-3'

(SEQ ID NO: 4)
Reverse primer: 5'-CTTTCTTGAGCCTGCGCTTC-3'

β-Actin:
(SEQ ID NO: 5)
Forward primer: 5'-AGCCATGTACGTAGCCATCC-3'

(SEQ ID NO: 6)
Reverse primer: 5'-CTCTCAGCTGTGGTGCTGAA-3'

PCR amplified cDNA was separated by electrophoresis on 1.5% agarose gel and cDNA band was identified using G:BOX EF imaging system (Syngene). The results are shown in FIG. 3.

As shown in FIG. 3, it was observed that the expression of MyoD and myogenin mRNA was increased in L6 muscle cells by treating the hexane extract, the ethyl acetate extract, the ethanol extract, and the hot water extract of *Platycodon grandiflorum*. This verifies that the extracts of *Platycodon grandiflorum* of the present invention are excellent in promoting muscle differentiation in muscle cells.

Example 5

Figure 4:
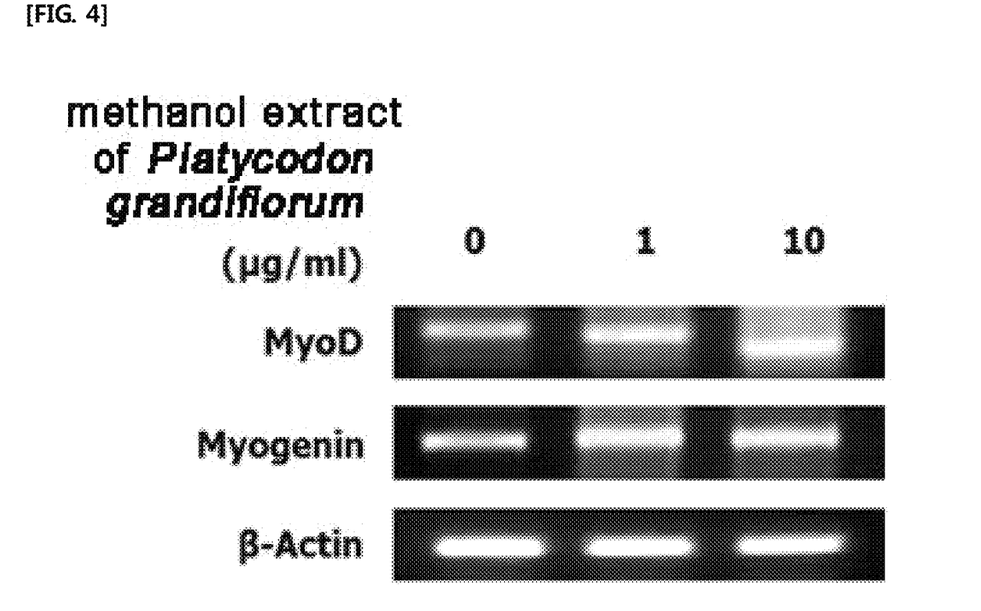
FIG. 4 shows the results of measuring the mRNA expression of MyoD and myogenin in L6 muscle cells by treating the methanol extract of *Platycodon grandiflorum*.

Effect of the Methanol Extract of *Platycodon grandiflorum* on Muscle Differentiation L6 myoblast (ATCC) was cultured in the same manner as in Example 4. The methanol extract of *Platycodon grandiflorum* prepared in Example 1-1 was dissolved in DMEM (Hyclone) containing 2% HS (Hyclone) at a concentration of 1 µg/mL and 10 µg/mL, followed by its treatment on said cells to induce myotube differentiation. Meanwhile, a group treated with 0.01% DMSO instead of the sample was used as a control group. RT-PCR was performed in the same manner as in Example 4, after proceeding for 6 days in 2 days to differentiate.

As shown in FIG. 4, it was observed that the expression of MyoD and myogenin mRNA was increased in L6 muscle cells by treating the methanol extract of *Platycodon grandiflorum*. This verifies that the methanol extract of *Platycodon grandiflorum* of the present invention is excellent in promoting muscle differentiation in muscle cells.

Example 6

Inhibitory Effect of *Platycodon grandiflorum* on Muscle Protein Degradation

L6 myoblast (ATCC) was added to a 6-well plate at $2\times10^5$ cells/ml together with DMEM (Hyclone) containing 10% FBS (Hyclone). When the cell density reached about 80% to 85%, the medium in the wells was removed and myotube differentiation was induced by treating the cells with DMEM (Hyclone) containing 2% HS (Hyclone). The medium was replaced with fresh medium every two days and the differentiation was carried out for a total of 6 days. After differentiation, 10 µg/mL of the hexane extract, the ethylacetate extract, the ethanol extract and the hot water extract of *Platycodon grandiflorum* prepared in Examples 1-2 to 1-5 were respectively dissolved in DMEM (Hyclone) containing 50 ng/mL tumor necrosis factor alph (TNF-α; PeproTech, Rocky Hills, N.J., USA), followed by their treatment on the cells. After 6 hours, total RNA was isolated using TRIzol reagent (Invitrogen). The isolated total RNA was quantified using NanoDrop 1000 (Thermo Fisher Scientific Inc.). The quantified 16 µL of RNA was synthesized into cDNA using Reverse Transcriptase Premix (ELPIS-Biotech) and PCR machine (Gene Amp PCR System 2700; Applied Biosystems) at 42° C. for 55 minutes and at 70° C. for 15 minutes. The PCR was performed by repeating 30 cycles at 95° C. for 30 seconds, at 60° C. for 1 minute and at 72° C. for 1 minute with 4 µl of 16 µl cDNA, the following specific primers (Bioneer), and PCR premix (ELPIS-Biotech):

```
Atrogin-1
                                       (SEQ ID NO: 7)
Forward primer: 5'-CCCTGAGTGGCATCGCCCAA-3'

(SEQ ID NO: 8)
Reverse primer: 5'-AGGTCCCGCCCATCGCTCA-3'

MuRF-1
                                       (SEQ ID NO: 9)
Forward primer: 5'-GAAATGCTATGCAGAACCTG-3'

(SEQ ID NO: 10)
Reverse primer: 5'-ATTCCTGCTTGTAGATGTCG-3'

β-Actin:
                                      (SEQ ID NO: 11)
Forward primer: 5'-AGCCATGTACGTAGCCATCC-3'

(SEQ ID NO: 12)
Reverse primer: 5'-CTCTCAGCTGTGGTGCTGAA-3'
```

PCR amplified cDNA was separated by electrophoresis on 1.5% agarose gel and cDNA band was identified using G:BOX EF imaging system (Syngene). The results are shown in FIG. 5.

Figure 5:
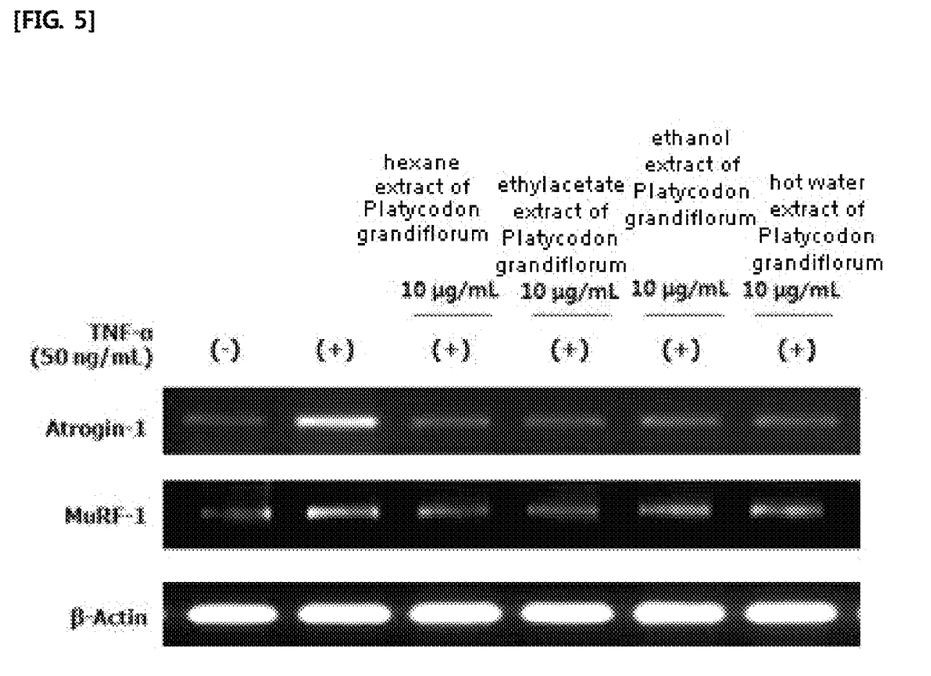
FIG. 5 shows the results of measuring the mRNA expression of atrogin-1 and MuRF-1 in L6 muscle cells by treating the hexane extract, the ethyl acetate extract, the ethanol extract, and the hot water extract of *Platycodon grandiflorum*.

As shown in FIG. 5, it was found that mRNA expression of atrogin-1 and MuRF-1 in L6 muscle cells was decreased by treating the *Platycodon grandiflorum* extracts. This verifies that the extracts of *Platycodon grandiflorum* of the present invention are excellent in inhibiting the degradation of muscle proteins in muscle cells.

Example 7

Effect of the High Pressure Extracts of *Platycodon grandiflorum* on Muscle Formation The ultra-high pressure extract of *Platycodon grandiflorum* prepared in Example 1-6, the supercritical fluid extract of *Platycodon grandiflorum* prepared in Example 1-7, and the subcritical fluid extract of *Platycodon grandiflorum* prepared in Example 1-8 were respectively treated at a concentration of 20 ppm on muscle cells in the same manner as in Example 2. The p-mTOR protein band was developed using ECL Western Blotting Detection Reagents (Amersham, Tokyo, Japan) and a density of the developed protein band was measured using G:BOX EF imaging system (Syngene, Cambridge, UK). The density of the relative protein bands in the experimental groups treated with the samples was expressed as a percentage (%) based on the protein band of the control group of which density is designated as 100%. The results are shown in Table 1 below.

TABLE 1

Effect of the high pressure extracts of *Platycodon grandiflorum* in enhancing the expression level of p-mTOR protein

| Experimental groups | Relative density (%) |
| --- | --- |
| Control group | 100 |
| Example 1-6 | 130 |
| Example 1-7 | 127 |
| Example 1-8 | 136 |

As shown in the Table 1, it was confirmed that the ultra-high pressure extract, the supercritical fluid extract, and the subcritical fluid extract of *Platycodon grandiflorum* respectively enhanced the protein expression level of p-mTOR which is a major gene involved in the improvement of muscle function.

Example 8

Evaluation on the Effect of Increasing Muscle Mass in Animal Models

Five-week-old Wistar rats were adapted for 1 week and 100 ng/g of TNF-α was supplied for 2 weeks to induce muscular atrophy. Then, groups were randomly assigned on the basis of body weight and divided into three groups of 8 rats per each group. 500 mg/kg body weight of the ethanol extract of *Platycodon grandiflorum* prepared in Example 1-2 and 500 mg/kg body weight of the hot-water extract of *Platycodon grandiflorum* prepared in Example 1-5 were suspended in 0.25% carboxymethylcellulose, respectively. Experimental groups were administrated with each suspended extracts once a day for 8 weeks at regular time. A control group was administered with TNF-α suspended in the same amount of 0.25% carboxymethyl cellulose ingested by the experimental groups.

After 8 weeks of administration, the muscles under the right calf were excised and weighed with microbalance (Mettler PE 160, USA). As a result, as shown in Table 2, the weight of muscle was significantly (p<0.01) increased by 21.18% and 18.23% in the group administered with the ethanol extract and the hot-water extract of *Platycodon grandiflorum*, respectively. These results indicate that the extracts of *Platycodon grandiflorum* according to the present invention are effective for increasing muscle mass.

TABLE 2

Weight of calf muscle per treated material

| Experimental groups | Average weight of calf muscle (mg) |
| --- | --- |
| Control group | 406 ± 20.3 |
| The ethanol extract *Platycodon grandiflorum* | 492 ± 31.6 |
| The hot water extract *Platycodon grandiflorum* | 480 ± 28.7 |

Hereinafter, there are disclosed preparation examples for preparing a pharmaceutical composition for preventing and treating muscle diseases, a food composition for preventing muscle diseases or improving muscle function, or a cosmetic composition for improving muscle function, the compositions comprising the *Platycodon grandiflorum* extract of Example 1 according to the present invention as an active ingredient. However, these preparation examples are not intended to be limiting the present invention by any means, but merely to be illustrative. The pharmaceutical, food or cosmetic compositions of Preparation Examples 1 to 3 were prepared according to the conventional methods using the following components and composition ratios.

<Preparation Examples 1> Food

<1-1> Preparation of Health Food 1000 mg of the *Platycodon grandiflorum* extract of Example 1, 70 μg of vitamin A acetate, 1.0 mg of vitamin E, 0.13 mg of vitamin B1, 0.15 mg of vitamin B2, 0.5 mg of vitamin B6, 0.2 μg of vitamin B12, 10 mg of vitamin C, 10 μg of biotin, 1.7 mg of Nicotinic amide, 50 μg of folic acid, 0.5 mg of calcium pantothenate, 1.75 mg of ferrous sulfate, 0.82 mg of zinc oxide, 25.3 mg of magnesium, carbonate, 15 mg of potassium monophosphate, 55 mg of dibasic calcium phosphate, 90 mg of potassium, citrate, 100 mg of calcium carbonate, and 24.8 mg of magnesium chloride may be mixed to prepare a health food, while the composition ratios may be modified. After mixing the above components according to general health food manufacturing methods, granules are prepared for use in the manufacture of a health food composition according to conventional methods.

<1-2> Preparation of Health Drinks 1000 mg of the *Platycodon grandiflorum* extract of Example 1, 1000 mg of citric acid, 100 g of oligosaccharide, 2 g of plum concentrate and 1 g of taurine were added to purified water, followed by mixing to obtain a total of 900 ml of health drink according to general health drink manufacturing methods. After stirring for about 1 hour at 85° C., the resulting solution was filtered and placed in a sterilized 2 L container, sealed, sterilized and refrigerated for use in the manufacture of a health drink composition.

<1-3> Chewing Gum

After mixing 20 wt % of gum base, 76.9 wt % of sugar, 1 wt % of flavor, 2 wt % of water and 0.1 wt % of the *Platycodon grandiflorum* extract of Example 1, chewing gum was prepared according to well-known methods in the art.

<1-4> Candy

After mixing 60 wt % of sugar, 39.8 wt % of starch syrup, 0.1 wt % of flavor and 0.1 wt % of the *Platycodon grandiflorm* extract of Example 1, candy was prepared according to well-known methods in the art.

<1-5> Biscuit

After mixing 25.59 wt % of first grade soft flour, 22.22 wt % of first grade plain flour, 4.80 wt % of refined sugar, 0.73 wt % of salt, 0.78 wt % of glucose, 11.78 wt % of palm shortening, 1.54 wt % of ammonium, 0.17 wt % of sodium bicarbonate, 0.16 wt % of sodium sulfite, 1.45 wt % of rice powder, 0.0001 wt % of vitamin B, 0.04 wt % of milk flavor, 20.6998 wt % of water, 1.16 wt % of whole milk powder, 0.29 wt % of alternative milk powder, 0.03 wt % of calcium phosphate I, 0.29 wt % of sulfuric salt, 7.27 wt % of spray milk and 1.0 wt % of the *Platycodon grandiflorum* extract of Example 1, biscuit was prepared according to well-known methods in the art.

<Preparation Example 2> Therapeutics

<2-1> Powder 50 mg of the *Platycodon grandiflorm* extract of Example 1 and 2 g of crystalline cellulose were mixed thoroughly and then, filled and sealed in a sealed package to obtain a powder preparation.

<2-2> Tablets 50 mg of the *Platycodon grandiflorm* extract of Example 1, 400 mg of crystalline cellulose and 5 mg of magnesium stearate were mixed thoroughly and formulated into tablet according to conventional methods to obtain a tablet preparation.

<2-3> Capsules 30 mg of the *Platycodon grandiflorum* extract of Example 1, 100 mg of whey protein, 400 mg of crystalline cellulose, and 6 mg of magnesium stearate were mixed thoroughly and filled in a gelatin capsule according to conventional methods to obtain a capsule preparation.

<Preparation Example 3> Cosmetics

<3-1> Nourishing Lotion (Milk Lotion)

According to conventional methods, nourishing lotion was prepared with the *Platycodon grandiflorum* extract of Example 1 and the following components at a ratio as shown in Table 3 below.

TABLE 3

| Composition ingredients | Preparation Example 3-1 (wt %) |
|---|---|
| *Platycodon grandiflorum* extract | 2.0 |
| Squalane | 5.0 |
| Wax | 4.0 |
| Polysorbate 60 | 1.5 |
| Sorbitan sesquioleate | 1.5 |
| Liquid paraffin | 0.5 |
| Caprylic/capric triglyceride | 5.0 |
| Glycerin | 3.0 |
| Butylene glycol | 3.0 |
| Propylene glycol | 3.0 |
| Carboxyvinyl polymer | 0.1 |
| Triethanolamine | 0.2 |
| Preservatives, Coloring, Fragrance | q.s. |
| Purified water | To 100 |

<3-2> Softening Lotion (Skin Lotion)

According to conventional methods, skin lotion was prepared with the *Platycodon grandiflorum* extract of Example 1 and the following components at a ratio as shown in Table 4 below.

TABLE 4

| Composition ingredients | Preparation Example 3-2 (wt %) |
|---|---|
| *Platycodon grandiflorum* extract | 2.0 |
| Glycerin | 3.0 |
| Butylene glycol | 2.0 |
| Propylene glycol | 2.0 |
| Carboxyvinyl polymer | 0.1 |
| PEG 12 Nonyl phenyl ether | 0.2 |
| Polysorbate 80 | 0.4 |
| Ethanol | 10.0 |
| Triethanolamine | 0.1 |
| Preservatives, Coloring, Fragrance | q.s. |
| Purified water | To 100 |

<3-3> Nourishing Cream

According to conventional methods, nourishing cream was prepared with the *Platycodon grandiflorum* extract of Example 1 and the following components at a ratio shown in Table 5 below.

TABLE 5

| Composition ingredients | Preparation Example 3-3 (wt %) |
| --- | --- |
| *Platycodon grandiflorum* extract | 2.0 |
| Polysorbate 60 | 1.5 |
| Sorbitan sesquioleate | 0.5 |
| PEG60 Hardened castor oil | 2.0 |
| Liquid paraffin | 10 |
| Squalane | 5.0 |
| Caprylic/capric triglyceride | 5.0 |
| Glycerin | 5.0 |
| Butylene glycol | 3.0 |
| Propylene glycol | 3.0 |
| Triethanolamine | 0.2 |
| Preservatives | q.s. |
| Coloring | q.s. |
| Fragrance | q.s. |
| Purified water | To 100 |

<3-4> Massage Cream

Massage cream was prepared according to conventional methods by using the *Platycodon grandiflorum* extract of Example 1 and the following components at a ratio as shown in Table 6 below.

TABLE 6

| Composition ingredients | Preparation Example 3-4 (wt %) |
| --- | --- |
| *Platycodon grandiflorum* extract | 1.0 |
| Wax | 10.0 |
| Polysorbate 60 | 1.5 |
| PEG60 Hardened castor oil | 2.0 |
| Sorbitan sesquioleate | 0.8 |
| Liquid paraffin | 40.0 |
| Squalane | 5.0 |
| Caprylic/capric triglyceride | 4.0 |
| Glycerin | 5.0 |
| Butylene glycol | 3.0 |
| Propylene glycol | 3.0 |
| Triethanolamine | 0.2 |
| Preservatives, coloring, fragrance | q.s. |
| Purified water | To 100 |

<3-5> Packs

A pack was prepared according to conventional methods at a composition ratio shown in Table 7 below.

TABLE 7

| Composition ingredients | Preparation Example 3-5 (wt %) |
| --- | --- |
| *Platycodon grandiflorum* extract | 1.0 |
| Polyvinyl alcohol | 13.0 |
| Sodium carboxymethylcellulose | 0.2 |
| Glycerin | 5.0 |
| Allantoin | 0.1 |
| Ethanol | 6.0 |
| PEG12 nonyl phenyl ether | 0.3 |
| Polysorbate 60 | 0.3 |
| Preservatives, coloring, fragrance | q.s. |
| Purified water | To 100 |

<3-6> Gels

A gel was prepared according to conventional methods by using the *Platycodon grandiflorum* extract of Example 1 and the following components at a ratio shown in Table 8 below.

TABLE 8

| Composition ingredients | Preparation Example 3-6 (wt %) |
| --- | --- |
| *Platycodon grandiflorum* extract | 0.5 |
| Ethylenediamine sodium acetate | 0.05 |
| Glycerin | 5.0 |
| Carboxyvinyl polymer | 0.3 |
| Ethanol | 5.0 |
| PEG60 Hardened castor oil | 0.5 |
| Triethanolamine | 0.3 |
| Preservatives, Coloring, Fragrance | q.s. |
| Purified water | To 100 |

What is claimed is:

1. A method for treating a muscle disease in a subject or improving a muscular function in a subject having the muscle disease, the method comprising administering an effective amount of a composition consisting of a *Platycodon grandiflorum* extract as an active ingredient to the subject in need thereof.

2. The method of claim 1, wherein the *Platycodon grandiflorum* extract is an extract obtained by using at least one solvent selected from the group consisting of water, an organic solvent having 1 to 6 carbon atoms, a subcritical fluid, a supercritical fluid, and a mixture thereof.

3. The method of claim 2, wherein the organic solvent having 1 to 6 carbon atoms is selected from the group consisting of alcohol having 1 to 6 carbon atoms, acetone, ether, benzene, chloroform, ethyl acetate, methylene chloride, hexane, cyclohexane, and petroleum ether.

4. The method of claim 1, wherein the muscle disease is selected from the group consisting of atony, muscular atrophy, muscular dystrophy, muscular degeneration, muscular spasticity, amyotrophic lateral sclerosis, myasthenia gravis, cachexia and sarcopenia.

5. The method of claim 1, wherein the *Platycodon grandiflorum* extract is obtained by extracting *Platycodon grandiflorum* under an ultra-high pressure of 100 MPa to 1000 MPa.

6. A method for treating a muscle disease in a subject or improving a muscular function in a subject having the muscle disease, the method comprising administering an effective amount of a composition comprising a *Platycodon grandiflorum* extract as an active ingredient to the subject in need thereof, wherein the *Platycodon grandiflorum* extract is an extract obtained by using at least one solvent selected from the group consisting of water, an organic solvent having 1 to 6 carbon atoms, a subcritical fluid, a supercritical fluid, and a mixture thereof.

7. The method of claim 6, wherein the organic solvent having 1 to 6 carbon atoms is selected from the group consisting of alcohol having 1 to 6 carbon atoms, acetone, ether, benzene, chloroform, ethyl acetate, methylene chloride, hexane, cyclohexane, and petroleum ether.

8. A method for treating a muscle disease in a subject or improving a muscular function in a subject having the muscle disease, the method comprising administering an effective amount of a composition comprising a *Platycodon grandiflorum* extract as an active ingredient to the subject in need thereof, wherein the *Platycodon grandiflorum* extract is obtained by extracting *Platycodon grandiflorum* under an ultra-high pressure of 100 MPa to 1000 MPa.

\* \* \* \* \*

SEQUENCE LISTING

<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: MyoD primer forward

<400> SEQUENCE: 1
tttcgactca ccagacctgc                                           20

<210> SEQ ID NO 2
<211> LENGTH: 20
<212> TYPE: DNA
<213> ORGANISM: Artificial Sequence
<220> FEATURE:
<223> OTHER INFORMATION: MyoD primer reverse

<400> SEQUENCE: 2
cagagcctgc agaccttcaa                                           20

```
<210> SEQ ID NO 3
<211> LENGTH: 20
<212> TYPE: DNA
<213> ORGANISM: Artificial Sequence
<220> FEATURE:
<223> OTHER INFORMATION: Myogenin primer forward

<400> SEQUENCE: 3
tttcgcacct gatggacctg                                          20

<210> SEQ ID NO 4
<211> LENGTH: 20
<212> TYPE: DNA
<213> ORGANISM: Artificial Sequence
<220> FEATURE:
<223> OTHER INFORMATION: Myogenin primer reverse

<400> SEQUENCE: 4
ctttcttgag cctgcgcttc                                          20

<210> SEQ ID NO 5
<211> LENGTH: 20
<212> TYPE: DNA
<213> ORGANISM: Artificial Sequence
<220> FEATURE:
<223> OTHER INFORMATION: beta-actin primer forward

<400> SEQUENCE: 5
agccatgtac gtagccatcc                                          20

<210> SEQ ID NO 6
<211> LENGTH: 20
<212> TYPE: DNA
<213> ORGANISM: Artificial Sequence
<220> FEATURE:
<223> OTHER INFORMATION: beta-actin primer reverse

<400> SEQUENCE: 6
ctctcagctg tggtgctgaa                                          20

<210> SEQ ID NO 7
<211> LENGTH: 20
<212> TYPE: DNA
<213> ORGANISM: Artificial Sequence
<220> FEATURE:
<223> OTHER INFORMATION: Atrogin-1 primer forward

<400> SEQUENCE: 7
ccctgagtgg catcgcccaa                                          20

<210> SEQ ID NO 8
<211> LENGTH: 19
<212> TYPE: DNA
<213> ORGANISM: Artificial Sequence
<220> FEATURE:
<223> OTHER INFORMATION: Atrogin-1 primer reverse

<400> SEQUENCE: 8
aggtcccgcc catcgctca                                           19

<210> SEQ ID NO 9
<211> LENGTH: 20
<212> TYPE: DNA
<213> ORGANISM: Artificial Sequence
<220> FEATURE:
```

-continued

```
<223> OTHER INFORMATION: MuRF-1 primer forward

<400> SEQUENCE: 9
gaaatgctat gcagaacctg                                              20

<210> SEQ ID NO 10
<211> LENGTH: 20
<212> TYPE: DNA
<213> ORGANISM: Artificial Sequence
<220> FEATURE:
<223> OTHER INFORMATION: MuRF-1 primer reverse

<400> SEQUENCE: 10
attcctgctt gtagatgtcg                                              20
```